(12) United States Patent
Multhoff et al.

(10) Patent No.: US 6,261,839 B1
(45) Date of Patent: Jul. 17, 2001

(54) METHOD FOR THE INDUCTION OF A NK CELL-MEDIATED IMMUNE RESPONSE

(75) Inventors: Gabriele Multhoff; Claus Botzler, both of München (DE)

(73) Assignee: GSF-Forschungszentrum fur Umwelt und Gesundheit GmbH, Oberschleissheim (DE)

( * ) Notice: Subject to any disclaimer, the term of this patent is extended or adjusted under 35 U.S.C. 154(b) by 0 days.

(21) Appl. No.: 09/273,616

(22) Filed: Mar. 22, 1999

(30) Foreign Application Priority Data

Mar. 27, 1998 (DE) ................................................ 198 13 759

(51) Int. Cl.$^7$ ........................................................ C12N 5/00
(52) U.S. Cl. ........................ 435/373; 435/325; 435/366; 435/372; 424/93.7; 424/93.71
(58) Field of Search ................................... 435/325, 235.1, 435/236, 254.1, 373, 372, 366; 424/93.7, 93.71

(56) References Cited

PUBLICATIONS

Botzler et al. International Journal of Cancer. 65(5). pp 633–638, 1996.*

* cited by examiner

Primary Examiner—Leon B. Lankford, Jr.
(74) Attorney, Agent, or Firm—Fish & Richardson P.C.

(57) ABSTRACT

According to the present invention, there is provided a method for the induction of a NK cell-mediated immune response ex vivo characterized in that a physiological cell suspension containing at least tumor cells or animal or human cells infected by viruses, bacteria and/or fungi (target cells) and NK cells is treated by the following process steps in the order mentioned to increase the sensitivity of the target cells for lysis by NK cells: Heat treating the cells contained in the suspension at a temperature of 38° C. to 43° C. for a period of at least 1 hour; lowering the temperature to physiological cell temperature (about 37° C.) to give the cells contained in the suspension a recovery period of at least 1 hour; addition of a compound increasing the portion of membrane-bound Hsp70 of the target cells in a concentration which is sublethal for the cells and allowing the compound to be effective for at least 30 minutes; recovery period of at least about 1 hour at 37° C.

20 Claims, 6 Drawing Sheets

2-LP

ET-18-OCH3

Tween20

METHOD FOR THE INDUCTION OF A NK CELL-MEDIATED IMMUNE RESPONSE

Figure 1:
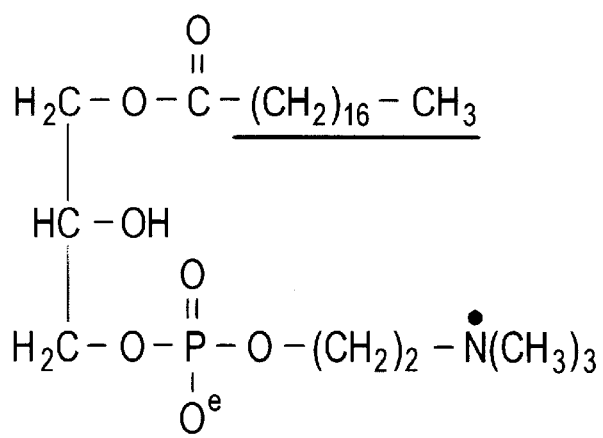
Figure 1:
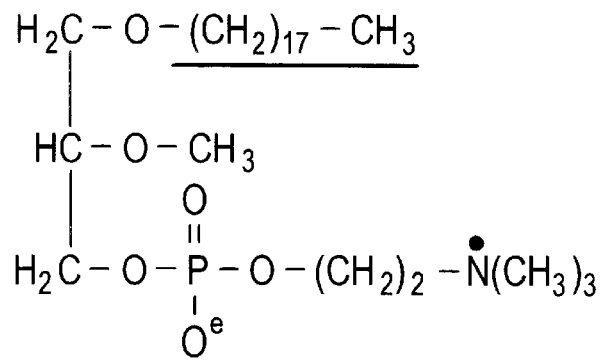
Figure 1:
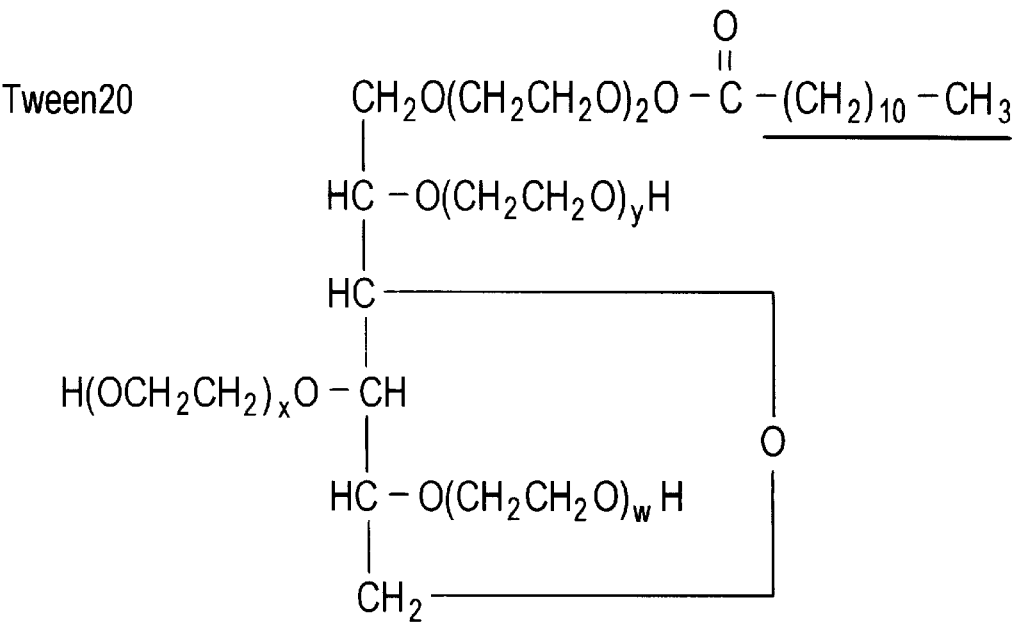

The present invention relates to an ex vivo method for the induction of a NK cell-mediated immune response and a method of treating diseases caused by viruses, bacteria and fungi and tumor diseases.

Etherlipids such as 1-octadecyl-2-methyl-rac-glycero-3-phosphocholine (ET-18-OCH3, edelfosine) belong to the group of alkyl-lysophospholipids. Alkyl-lysophospholipids are synthetic analogs of the naturally occuring 2-lyso phosphatidylcholine. It has been known that alkyl-lysophospholipids are cytotoxic and selectively kill neoplastic cells. It has been known that at cytotoxic concentrations of alkyl-lysophospholipids tumor cell growth is inhibited in vitro and in vivo by direct destruction of tumor cells.

Although the mechanism of cytotoxicity induced by etherlipids is unknown it is believed that the plasma membrane is a main target of the cytotoxic activity of alkyl-lysophospholipids, e.g. of ET-18-OCH3. Thus, for example, it has been shown that by alkyl-lysophospholipid derivatives the membrane permeability, membrane fluidity, lipid composition of the membrane and its cholesterol content are affected. Furthermore, ET-18-OCH3 has been employed as a purging agent in preclinical models of autologous hematopoietic stem cell transplantation and in clinical phase I/II studies in the ex vivo purging.

However, it has been observed that e.g. some leukemic cell lines, for example K562, are relatively resistant against ET-18-OCH3-mediated cytotoxic effects (1). Therefore, a purging treatment could be associated with a higher risk for a new outbreak of the leukemic disease due to the reinfusion of highly resistant leukemic cells into the patient. To avoid this drawback and to increase the cytotoxic effects of ET-18-OCH3 other methods of treatment have been suggested in addition, for example a hyperthermal treatment to be conducted in vitro ((2)–(4)). Thus, the publication (2) discloses the treatment of HL-60, K562, and KG-1 leukemic cells from the bone marrow of leukemic patients with 50 $\mu$g/ml ET-18-OCH3 and a subsequent heat shock treatment at 42° C. for one hour. This achieves a direct cytotoxic effect on the tumor cells.

From (3) there has been known the treatment of BG-1 ovarian carcinoma cells with 1, 2, and 4 $\mu$M of ET-18-OCH3, respectively, (1 $\mu$m is equivalent to about 0.5 $\mu$g/ml) for a period of 1–12 days and a subsequent heat shock treatment at 42° C. or 44° C., respectively. This method kills the tumor cells by direct cytotoxic effects.

From (4) there has been known the treatment of BG1 cells with ET-18-OCH3 at a concentration of 2 and 8 $\mu$M, respectively, followed by a heat shock treatment at 42° C. for a period of 0–16 hours and at 44° C. for a period of 0–33 hours. This is said to be effective in achieving a direct enhanced cytotoxic effect on the tumor cells.

From (5) it has been known that upon non-toxic treatment of K562 cells with ET-18-OCH3 a significant increase in sensitivity of K562 cells for the lysis by interleukin-2-stimulated NK cells occurs. Moreover, this reference reports that similar effects may be achieved by a non-lethal heat shock treatment. However, the combination of the two methods of treatment and the imperative observance of a certain order in the treatment to achieve a stimulation of the cytolytic activity of NK cells for tumor cells or a synergistic effect is not suggested therein.

It is an object of the present invention to provide a method which is useful ex vivo for the induction of a NK cell-mediated immune response. Said method will be furthermore designed to render the cell suspension thus treated reinfusable into the patient for treatment of the tumor disease.

According to the invention this object has been solved by the method according to claim 1 of the appended claims. Preferred embodiments of the method arise from the dependent claims as well as the following specification and the examples.

The method according to the invention is effective in inducing an immune response mediated by natural killer cells. For this purpose a physiological cell suspension containing at least tumor cells or animal or human cells infected by viruses, bacteria and/or fungi, shortly referred to as target cells, and natural killer cells is treated by the following process steps in the order mentioned to increase the sensitivity of the target cells for lysis by NK cells:

a) Heat treating the cells contained in the suspension at a temperature of 38° C. to 43° C. for a period of at least one hour;

b) lowering the temperature to physiological cell temperature (about 37° C.) to give the cells contained in the suspension a recovery period of at least one hour;

c) addition of a compound increasing the portion of membrane-bound Hsp70 of the target cells in a concentration which is sublethal for the cells and allowing the compound to be effective for at least 30 minutes;

d) recovery period of at least 1 hour at 37° C.

Thus, according to the invention a method is provided for increasing the lytic activity of NK cells for tumor cells, in particular for leukemic cells, lymphoma cells, and cells derived from metastases of solid tumors. Futhermore, by the method according to the invention also cells may be effectively lysed which are infected by viruses, bacteria, and/or fungi. Also cells containing antigenic portions of these foreign organisms or tumor cells may be lysed by the method of the invention while the lysis is mediated by an increase in sensitivity of the target cells to an attack by NK cells.

The method of the invention achieving an increase in sensitivity of the target cells for lysis by natural killer cells is characterized in that a physiological cell suspension containing at least the target cells and natural killer cells under strict observance of a specific order is subjected to a combination of first a heat treatment, followed by a recovery phase after which a treatment with a sublethal concentration of a compound is performed which increases the portion of membrane-bound Hsp70 of the target cells. According to the invention, an alkyl-lysophospholipid is used as the compound increasing the portion of membrane-bound Hsp70 of the target cells. This is followed by another recovery phase. Using the method of the invention, a marked increase in sensitivity of the target cells for lysis by NK cells is achieved.

The NK cells may be isolated from the patient to be treated or a healthy donor by suitable methods. Preferably, however, the NK cells are present together with other peripheral mononucleated blood cells, for example in the form of buffy coat cells.

Buffy coat cells are obtained from the patient via the vein and are for example added with heparin to avoid aggregation of the cells. The whole blood added with heparin is collected in a sterile container (mostly a plastic bag) and is then centrifuged to achieve an enrichment of blood cells (=PBMC, peripheral mononucleated cells, e.g. lymphocytes, erythrocytes, granulocytes etc.). A major portion of the serum ($\frac{2}{3}$) is removed in sterile manner and stored for the patient who for example has to undergo surgery and may need his own serum. The lymphocyte concentrate remains in the container (plastic bag). In the case of healthy subjects a buffy coat consists of white and red blood cells (lymphocytes, erythrocytes etc.). In the case of a tumor patient the buffy coat consists not only of blood cells but also contains tumor cells (in the case of leukemia: leukemic cells=blasts; in the case of solid tumors e.g. metastases in the form of single cells).

The whole blood or the buffy coat cells containing peripheral mononucleated blood cells are employed in the form of a physiological cell suspension, preferably added with heparin. Heparin functions to inhibit the aggregation of cells.

There has been provided completely unexpected evidence as demonstrated herein using K562 leukemia cells as an example which exhibit a strong resistance against treatment with a compound increasing the portion of membrane-bound Hsp70 in the target cell, such as an alkyl-lysophospholipid, that the target cells can be significantly more easily lysed by a combination of heat and ALP treatments in the oder indicated.

Figure 2:
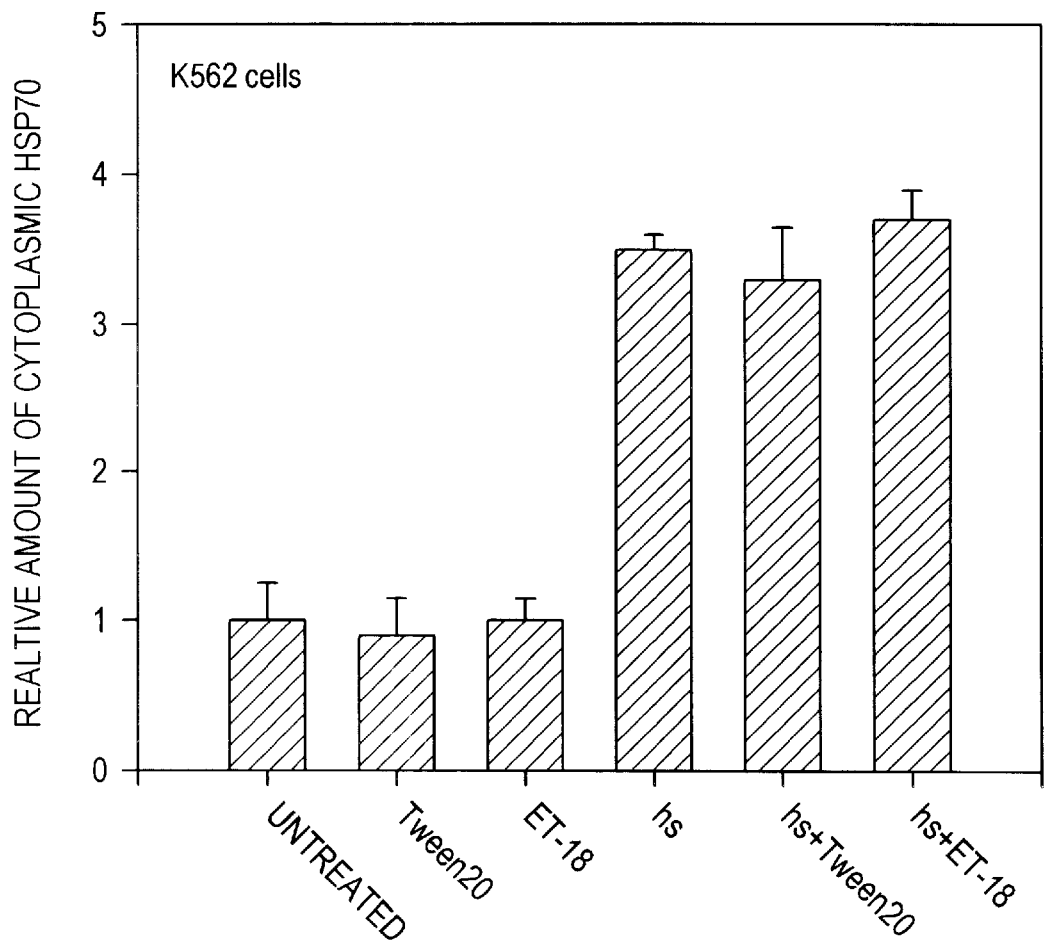

In particular, it has been demonstrated that if the heat treatment and the treatment with alkyl-lysophospholipids is carried out simultaneously no synergistic stimulation of the lysis by natural killer cells occurs. Performing the treatment by e.g. an alkyl-lysophospholipid first and carrying out a hyperthermal treatment afterwards was also unsuccessful (FIG. 2).

It was not before both methods were combined in the order claimed according to the invention, namely first performing a heat treatment and afterwards a treatment with a sublethal concentration of e.g. an alkyl-lysophospholipid, wherein the heat treatment and the alkyl-lysophospholipid treatment each must be followed by a recovery phase of sufficient length of at least one hour for the cells that the success was achieved which is highly desired by the patient but was unexpected with regard to the known prior art. In designing the experiments performed according to the invention it also became clear that the relative increase in membrane-bound Hsp70 protein upon combining an alkyl-lysophospholipid treatment and a heat treatment was not only additive but hyperadditive, i.e. synergistic. A synergistic increase in membrane-bound Hsp70 of that type by the method of the invention was unexpected. It should be noted that Hsp70 protein is equivalent to Hsp72 protein and is the protein of the Hsp70 family which is most strongly induced by heat. In the treatment according to the invention, i.e. a combination of a heat treatment with e.g. a treatment with alkyl-lysophospholipids, membrane expression of Hsp70 is achieved exclusively in the target cells while normal blood cells, also those of the patients, show no or at least no increase in Hsp70 membrane expression. The expression of Hsp70 on the target membrane of the target cells, e.g. the tumor cells, is a recognition signal for the lysis by NK cells.

Heat treatment of the target cells present in a cultur liquid together with natural killer cells (NK cells) takes place by increasing the temperature between 38° C. to 43° C., for example to 40° C.–42° C. Higher temperatures are preferred. However, it should be understood that the temperature should not be too high to effect a lethal damage of the cells since too many dead cells must not be reinfused into the patient. The heat treatment is performed for a period which is sufficient to induce the formation of heat shock proteins, preferably Hsp70, in the cell. It is preferred to perform the heat treatment for at least one hour while a time from up to three hours has been useful. Depending on the target cells to be treated, however, also other periods and other temperatures may be used. These may be determined by the skilled artisan by experimentation without inventive step.

It is crucial to keep the recovery periods. The recovery period following heat treatment should be at least for one hour and the recovery period following treatment with e.g. an alkyl-lysophospholipid should be at least for one hour, and they may for example last for up to 16 hours. It has been shown that preferred durations of the recovery periods of 8 to 12 hours are suitable. However, depending on the cells to be treated also other durations may be used. The temperature during the recovery period is preferably the physiological temperature of the cells, preferably about 37° C.

Treatment of the target cells with e.g. the alkyl-lysophospholipid is done with a concentration in the sublethal range so that the cells will not be lethally damaged. The sublethal concentration of the alkyl-lysophospholipid in the case of K562 cells which are used as an example in the present invention is in the range of 10–30 $\mu$g/ml. A suitable range is 15–25 $\mu$g/ml, furthermore 15–20 $\mu$g/ml or 10–25 $\mu$g/ml. Depending on the target cells to be treated also other concentrations may be used which may be determined by experimentation without an inventive step.

Preferably, for the method of treatment according to the invention alkyl-lysophospholipids are used. Alkyl-lysophospholipids are known per se and are for example described in (10). Examples are ES-18-OCH3 (lysophosphatidylcholine), BN52205, BN52207, BN52208, BN52211. However, also other compounds different from the alkyl-lysophospholipids cited may be used with the proviso that they are capable of increasing the portion of membrane-bound Hsp70 of the target cells.

By the method of the invention it is possible to kill tumor cells. Preferably, leukemic cells and tumor cells derived from metastases of solid tumors will be lysed. Examples of leukemic cells are K562 cells or lymphoma cells. Examples of tumor cells derived from metastases of solid tumors are carcinoma cells, sarcoma cells, and melanoma cells. Examples for these are ovarian carcinoma cells, colon carcinoma cells, adenocarcinoma cells, mamma carcinoma cells, and epidermoid carcinoma cells. Furthermore, by the method of the invention also human or animal cells may be killed or lysed, respectively, which are infected by viruses, bacteria and/or fungi. These cells are commonly referred to as target cells. Furthermore, also those cells may be attacked by the NK cell-mediated immune reaction which contain antigenic portions of such viruses, bacteria and/or fungi or tumor cells.

Examples for such cells infected by viruses are HIV infected cells. Examples for such cells infected by bacteria are cells infected by mycobacteria.

In the following, the invention will be described in more detail with respect to the examples and the accompanying drawings. The examples are merely understood as illustrative of the invention, and the invention is not limited to these examples. It should be understood that variations of the invention in the frame of the present specification and the claims are possible and are comprised in the scope of the claims of the invention.

THE ACCOMPANYING FIGURES AND TABLES SHOW

Table 1: The viability of K562 leukemic cells in comparison to PBL cells and CD34-positive progenitor cells derived from healthy donors following a combination treatment with a non-lethal heat dose (at 41.8° C., 2 hours) and ET-18-OCH3 or Tween 20 in varying concentrations.

The viability is indicated as the percentage of surviving cells and is determined by trypane blue dye exclusion staining. CD34-positive progenitor cells were not treated with Tween 20 since the amount of cells obtained from a donor was not sufficient for all of the tests. The values represent mean values of three independent experiments; n.t. indicates "not tested", i.e. no experiments were performed.

Table 2: The membrane expression of Hsp70 on PBL and CD34-positive progenitor cells (purity>90%) either without treatment or with a subsequent treatment with ET-18-OCH3, 25 μg, heat (41.8° C., 2 hours) or heat plus ET-18-OCH3. The results are given as the difference in percentage of cells with Hsp70 positive staining minus the percentage of cells stained by a control antibody corresponding to the isotype. Only viable propidium iodide-negative cells were analysed by a FACScan device. The values given represent mean values of three independent experiments±standard deviation (SD).

Table 3: The calculation of specific differences in the lysis of K562 cells either untreated (untr), heat treated (hs), treated with ET-18-OCH3 or treated with heat and ET-18-OCH3. The values represent mean values of three experiments±standard deviation (SD). * indicates values which differ significantly ($p<0.05$) from the control values, as calculated by the Student's t test.

Table 4: The calculation of specific differences in the lysis of PBL cells and cells enriched for CD34-positive cells (CD34-positive cells were in the range of 25%–45%) either without treatment (untr) or with a treatment by heat and ET-18-OCH3. The values represent mean values of two experiments±standard deviation (SD).

FIG. 1: The FIG. 1 shows the chemical structure of 2-lyso phosphatidylcholine (2-LP), 1-octadecyl-2-methyl-rac-glycero-3-phosphocholine (ET-18-OCH3) and polyoxyethylene sorbate 20 (Tween 20). Regions that are expected to interact with membranes are in bold and underlined.

FIG. 2: The cytoplasmic portion of Hsp70 in leukemic K562 cells may be increased neither by heat treatment nor by treatment with Tween 20. A comparison of the relative amount of Hsp70 in the cytoplasm of K562 cells shows:

untreated (lane 1), treated with Tween 20 (5 ppm, 2 hours; lane 2), treated with ET-18-OCH3 (25 μg/ml, 2 hours; lane 3), heat treated (41.8° C., 2 hours; lane 4), treated with heat and Tween 20 (lane 5), or treated with heat and ET-18-OCH3 (lane 6); or with ET-18 and heat (lane 7). The cell lysates were separated on a 10% SDS-PAGE under reducing conditions and transferred to a PVDF membrane. Hsp70 was detected by an antibody specific for Hsp70; the immunoblots were quantified by laser densitometry. The results are mean values of three independent experiments; the vertical lines indicate the standard deviation.

Figure 3:
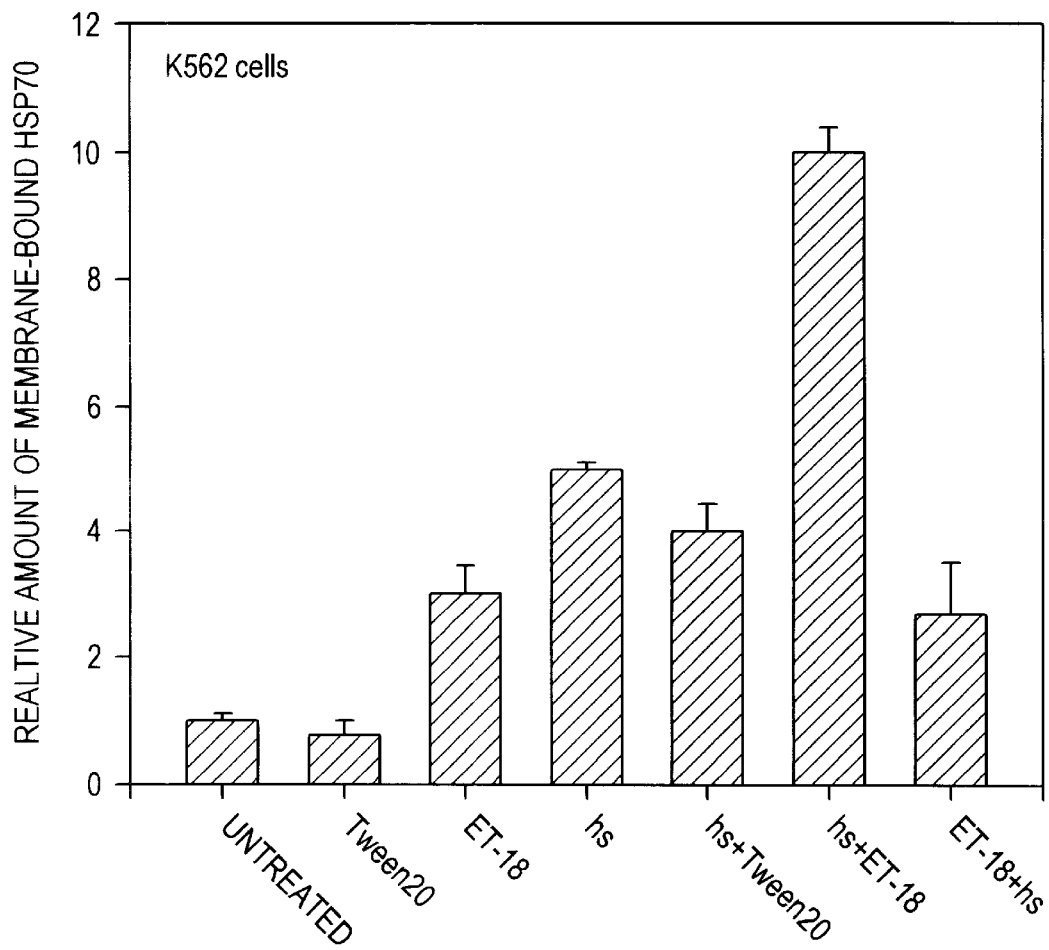

FIG. 3: Synergistic effect of heat and ET-18-OCH3 on the membrane expression of Hsp70. Comparison of the relative amount of membrane-bound Hsp70 in K562 cells: untreated (lane 1), treated with Tween 20 (5 ppm, 2 hours; lane 2), treated with ET-18-OCH3 (25 μg/ml, 2 hours; lane 3), heat treated (41.8° C., 2 hours; lane 4), treated with heat and Tween 20 (lane 5), or treated with heat and ET-18-OCH3 (lane 6); or with ET-18-OCH3 and heat (lane 7). Similar amounts of protein (10 μg) from K562 membrane lysates were separated on a 10% SDS-PAGE under reducing conditions and transferred to PVDF membrane. The band of the 72 kD heat shock protein was detected by a Hsp70-specific monoclonal antibody and using the ECL system. The immunoblots were quantified by laser densitometry. The results show the mean values of two independent experiments; the vertical lines indicate the standard deviation.

Figure 4:
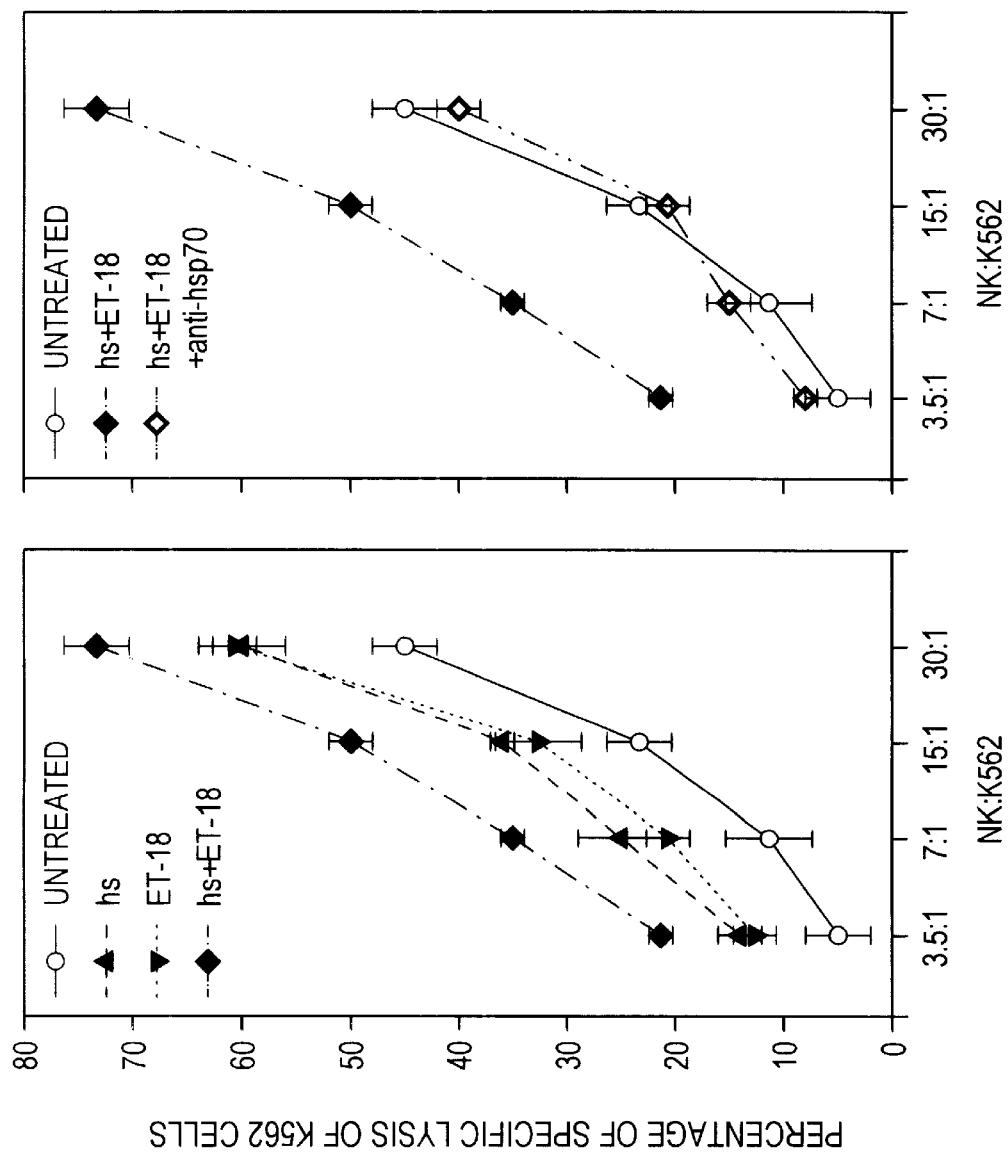

FIG. 4: Synergistic increase in sensitivity of lysis following treatment with heat and ET-18-OCH3. A comparison of the cytotoxic activity of an effector cell population enriched in NK cells against K562 leukemic cells after heat treatment (hs; 41.8° C., 2 hours), Tween 20 treatment (5 ppm), treatment by heat plus ET-18-OCH3 (hs+ET-18; 25 μg/ml), or treatment by heat plus Tween 20 (hs+Tween 20). The E:T (NK:K562) ratios were in the range of 3.5:1 to 30:1. Each value is the mean value of three independent experiments. A statistical analysis of differences in K562 cell lysis is presented in Table 2.

Figure 5:
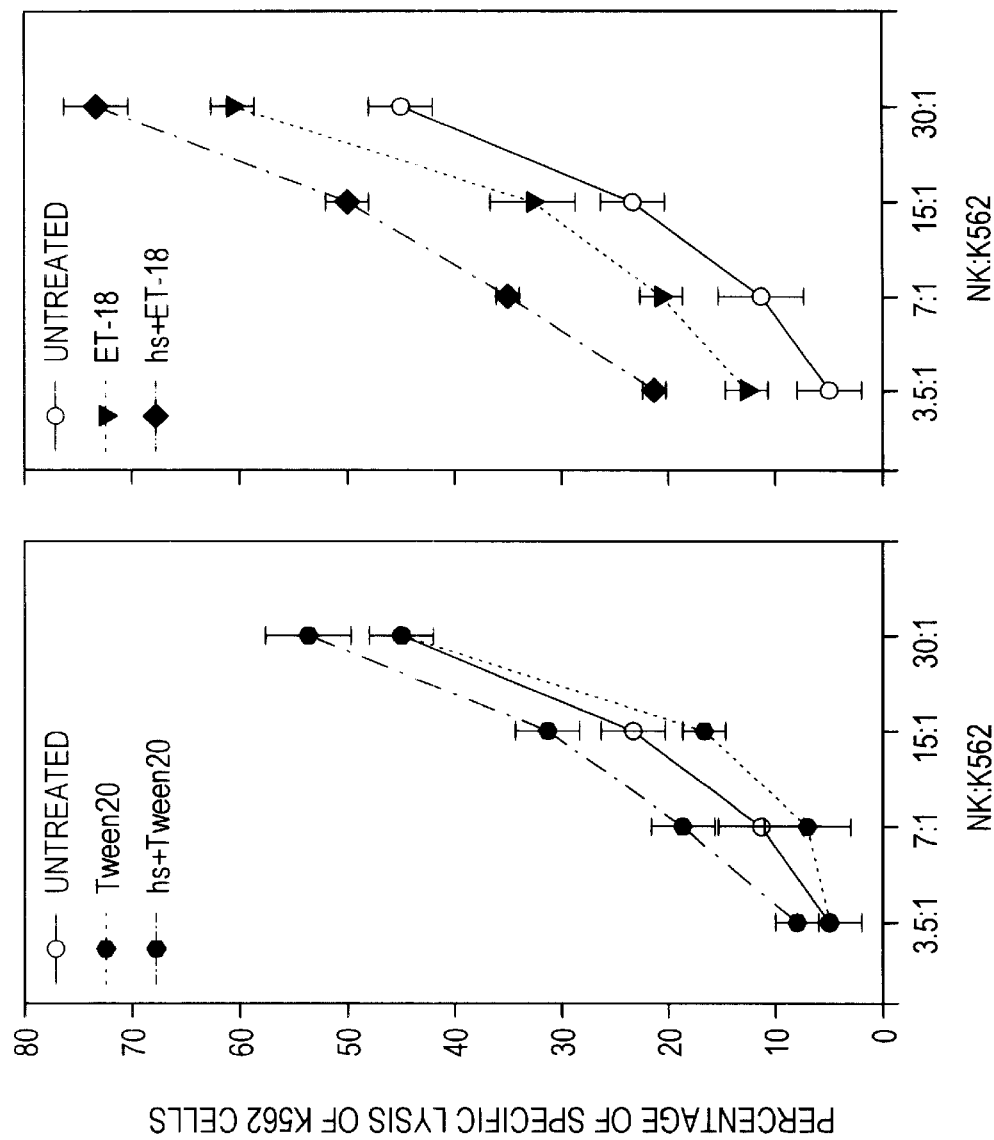

FIG. 5: The synergistic increase in sensitivity for lysis by the combination treatment according to the invention with heat and ET-18-OCH3 may be blocked by use of an antibody specific for Hsp70. A comparison shows the cytotoxic activity of an effector cell population enriched in NK cells compared with untreated, heat treated (hs; 41.8° C., 2 hours), or with heat treated and ET-18-OCH3 treated (hs+ET-18, 25 μg/ml) K562 leukemic cells. The E:T ratios (NK:K562) were in the range of 3.5:1 to 30:1. Each value is the mean value of three independent experiments. A statistical analysis of the differences in lysis of K562 cells is given in Table 2.

Figure 6:
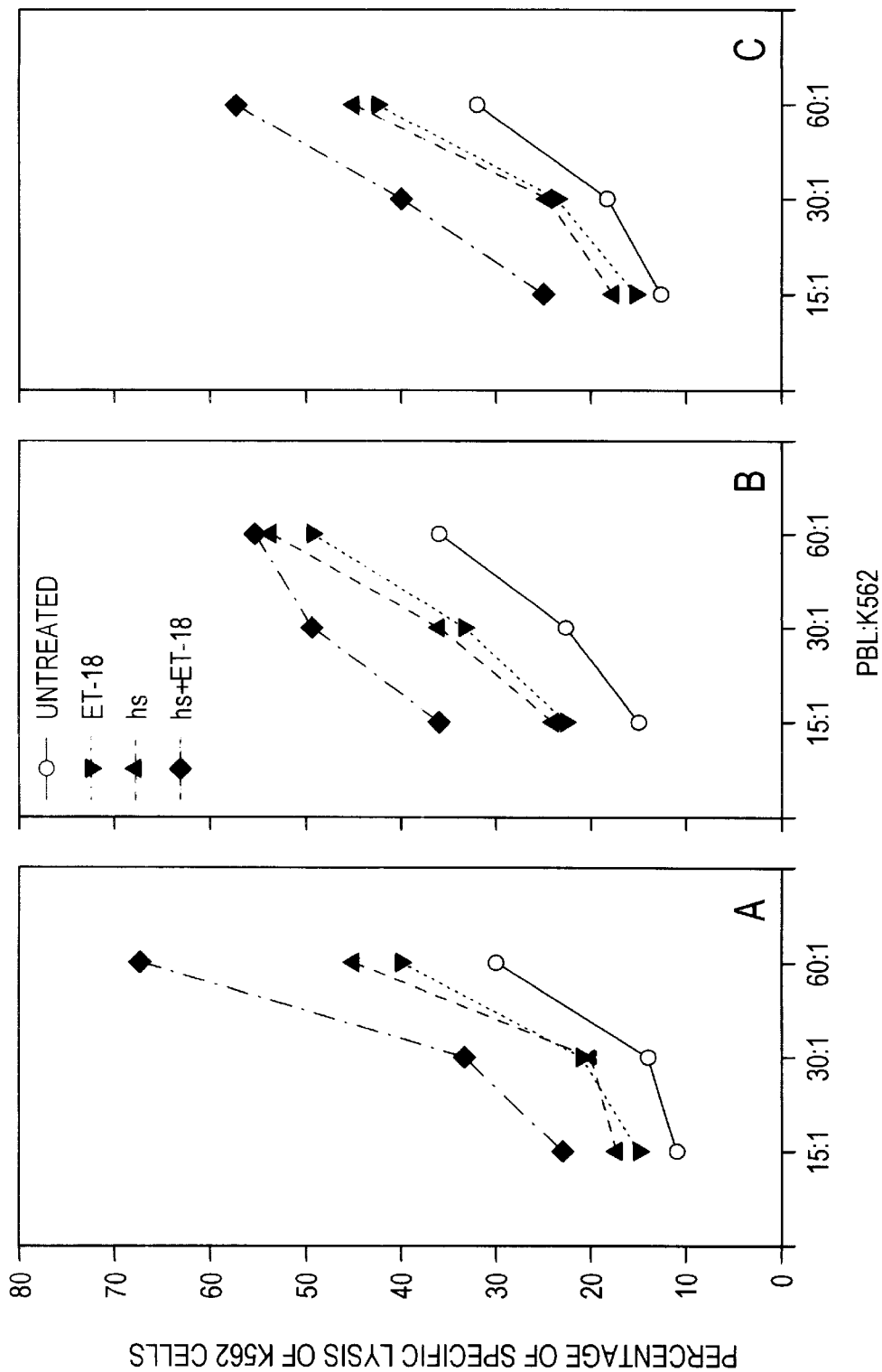

FIG. 6: Increased lysis in K562 cells treated with heat and/or ET-18 is mediated by unstimulated peripheral blood lymphocytes containing resting NK cells. A comparison of the cytotoxic activities of unstimulated effector cells derived from three HLA-distinct human donors (A, B, and C) compared to untreated, heat treated (hs; 41.8° C., 2 hours) or heat treated and ET-18-OCH3 treated (hs+ET-18; 25 μg/ml) K562 leukemic cells is shown. The E:T ratios (PBL:K562) were in the range of 15:1 to 60:1.

It has been surprisingly found out according to the present invention that by a combined treatment of target cells, e.g. tumor cells, with an increased temperature and a sublethal concentration of e.g. an alkyl-lysophospholipid in this order also such target cells, e.g. tumor cells, such as leukemic cells are rendered susceptible for cell lysis by natural killer cells (NK cells) which are attacked at a significant lower rate without this combined treatment. While according to the prior art alkyl-lysophospholipids are used in concentrations exhibiting a cell damage, i.e. direct, cytotoxic effect to directly kill the target cells, according to the present invention there is employed a substantially more gentle method which has no direct cytotoxic effect on the target cells but kills the target cells in an indirect immunological manner via NK cells by lysis.

Due to the experiments conducted according to the present invention the combined treatment of a sublethal heat shock and a non-cytotoxic concentration of an alkyl-lysophospholipid may be regarded as increasing the portion of membrane-bound heat shock proteins, in particular the membrane-bound heat shock protein Hsp70 on the target cells as demonstrated herein with respect to leukemic cells not only in an additive but in a synergistic manner. This increase in membrane-bound Hsp70 is most likely the reason for the synergistic increase in sensitivity of the target cells for lysis by NK cells taking place in the combination treatment of the target cells according to the invention by heat and alkyl-lysophospholipids in the order indicated (the finding is supported by antibody blocking experiments) (cf. FIGS. 4 and 5).

The NK cells mediating the lysis of the target cells are in particular characterized in that they express CD16 and/or may be stimulated by interleukin-2 and/or lack CD3 expression and/or have no $\alpha/\beta$ or $\gamma/\delta$ T cell receptors and/or are not dependent on the MHC type of the patient.

NK-cell Characteristics:

Transient plastics adherent following addition of IL-2 (Chiron, 100 I.U.):

The adhesion occurs 12–18 hours following addition of IL-2 to freshly isolated PBLs (peripheral blood lymphocytes depleted of monocytes);

the NK cells exhibit a CD16dim expression (mean fluorescence weak);

the NK cells express CD56 and CD57 as NK markers;

the NK cells express CD94 (C-type lectin killer cell receptor);

the NK cells secrete IFNgamma following activation;

not dependent on the MHC-type of the patient.

However, also other NK cell populations may be used provided that they lyse the tumor cells after the present treatment.

The method according to the present invention is preferably suitable for the treatment of leukemic cells. However, also other tumor diseases may be treated, preferably diseases asociated with solid tumors such as ovarian carcinomas, colon carcinomas, adenocarcinomas, epidermoid carcinomas and mamma carcinomas. However, also target cells may serve as the targets of attack. Examples therefor have been mentioned above.

The method according to the invention provides the possibility not only to directly kill tumor cells, such as leukemic cells, ex vivo in the context of a purging treatment but also to use the method in combination with hyperthermal treatment in vivo due the avoidance of cytotoxic concentrations of the etherlipid. Further, the present method has the inestimable and surprising advantage, that it is now possible to kill also target cells, e.g. tumor cells which were resistant to known methods of a hyperthermal treatment and treatment by etherlipids by the indirect effect via NK cells.

An example for the treatment using the method of the invention is as follows:

Buffy coat cells (lymphocyte concentrate) consisting of peripheral mononucleated blood cells or of bone marrow cells, and tumor cells from tumor patients, e.g. leukemia patients, are subjected a hyperthermal treatment in a container, e.g. a plastic container which is sealed in a sterile manner in a temperature controlled water bath. Following a recovery phase which may be performed in an incubator or a water bath at recovery temperature (preferably at physiological cell temperature, i.e. about 37° C.) an alkyl-lysophospholipid is added to the container in a sublethal concentration. In the container, there are tumor cells as well as NK cells which are stimulated by the present treatment. After completion of the method according to the present invention, the culture solution containing NK cells and the lysed tumor cells is reinfused back to the patient in an amount of about 100–1, 000×10$^6$, preferably about 200–800×10$^6$ lymphocytes.

As already detailed above, the NK cells are present according to the invention together with other peripheral mononucleated blood cells, e.g. together with erythrocytes and granulocytes and T cells. Thus, the NK cells are preferably not used alone, but are obtained by isolation of buffy coat cells and enrichment of peripheral mononucleated blood cells. In tumor patients, these enrichments further contain tumor cells, which can be treated by the method according to the present invention.

In particular, the treatment strategy is directed to the elimination of single cell metastases which can be immunologically eliminated by means of the method according to the present invention. An enhanced activation of Hsp70-specific NK cells can be achieved by addition of interleukin-2 in a low dose, for example 100 IU. For example, interleukin-2 may be introduced into the sterile container, e.g. a plastic container, together with the alkyl-lysophospholipid.

The method of the present invention has been developed with respect to a specific etherlipid, namely ET-18-OCH3, a synthetic derivative of the naturally occurring 2-lysophosphatidylcholine, in combination with the K562 leukemic cell line. However, it is also possible to perform the method with other leukemic cells and generally also other tumor cells and using other alkyl-lysophospholipids.

To investigate the non-toxic concentrations of ET-18-OCH3 in combination with a non-lethal temperature for peripheral blood lymphocyte cells (PBMC cells), K562 cells and CD34-positive stem cells, trypane blue or propidium iodide exclusion studies were carried out. Table 1 shows that a concentration of 25 μg/ml with ET-18-OCH3 in a medium containing 10% FCS and an incubation time of 2 hours were non-toxic for K562 cells. PBL cells as well as CD34-positive progenitor cells from healthy donors exhibited a similar resistance against the treatment with ET-18-OCH3. Furthermore it has been demonstrated that this non-toxic concentration of ET-18-OCH3 does not induce apoptosis in K562 cells. As a control, the membrane-interactive detergent Tween 20 has been used. It could be demonstrated that with an incubation time of 2 hours and a concentration of 5 μpm no cytotoxic effect on K562 cells, PBL cells and CD34 cells was observed (cf. Table 1). For all further investigations this non-lethal concentration was chosen.

To investigate if a combination of a non-lethal heat treatment, non-toxic ET-18-OCH3 concentrations (25 μg/ml for 2 hours) and Tween 20 (5 μpm for 2 hours) either alone or in combination with a heat treatment (41.8° C. for 2 hours) induces the synthesis of heat shock proteins (Hsp), the Hsp70 level in cytoplasm was determined. It has been found that neither Tween 20 nor ET-18-OCH3 alone increase the Hsp70 content in the cytoplasm. If K562 cells were only subjected to heat treatment, an about 2 fold increase in the cellular Hsp70 level in K562 cells occured. This increase was unaffected even if the cells were subjected to a combined treatment of heat and Tween 20 or heat and ET-18-OCH3 (cf. FIG. 2). Similar results were achieved using PBL cells from healthy donors as well as CD34-positive progenitor cells. Due to the lower initial amounts of Hsp70 in PBL cells and CD34 progenitor cells the increase of Hsp70 in the cytoplasm following heat treatment was more than 5 fold (data not shown).

In contrast to the induction of Hsp70 in the cytoplasm the portion of membrane-bound Hsp70 increased significantly after treatment with heat (41.8° C. for 2 hours), a recovery phase at 37° C. for 8 hours, and/or ET-18-OCH3 (25 μg/ml, 2 hours) and a recovery phase of 2 hours at 37° C. The portion of membrane-bound Hsp70 is increased by a treatment with ET-18-OCH3 alone by about 3 fold, by the heat treatment by 5 fold, and by a sequential/subsequent treatment of the cells with heat and then plus ET-18-OCH3 a more than 10 fold increase in the membrane-bound Hsp70 portion occurs. As compared to a heat treatment alone, a treatment of the K562 cells with ET-18-OCH3 and subsequent heat treatment does not result in a further increase in Hsp70 expression on the membrane (FIG. 3), i.e. the order of the treatments is important for success. Treatment of the cells with the membrane-interactive Tween 20 (5 ppm, 2 hours) alone showed no effect on the portion of membrane-bound Hsp70. In the combination with heat treatment, the effect was not higher than with heat alone.

Flow cytometric studies showed that PBL cells or CD34-positive progenitor cells as opposed to K562 cells failed to show Hsp70 plasma membrane expression either under physiological conditions or after a treatment with heat and/or ET-18-OCH3 (cf. Table 2). This provides evidence that the membrane expression of Hsp70 is a tumor-specific phenomenon.

To answer the question whether the more than 10 fold increase in the portion of membrane-bound Hsp70 in K562 cells by the combined treatment with heat and ET-18-OCH3 induces an increased sensitivity of the tumor cells for a lysis treatment, cytotoxicity tests were performed. As the effector cells, resting NK cells (=unstimulated PBLs) or IL-2-stimulated NK-enriched cell populations were used. As comparative test, a chromium release assay was used which was performed both in untreated K562 cells and in K562 cells subjected to a combined treatment of heat shock and ET-18-OCH3. The combined treatment with heat shock followed by ET-18-OCH3 treatment showed a significant ($p<0.05$) increase in sensitivity of the tumor cells for lysis as compared to the controls (about 2 fold increase). The lysis of K562 cells which had been treated with ET-18-OCH3 alone was increased by about 1.3 fold (Table 3); in tumor cells treated with Tween 20 alone no increase in lysis was observed as compared to the controls. Furthermore, also a combined treatment of K562 cells with heat plus Tween 20 did not result in an increased lysis portion compared to the lysis with only heat shock-treated K562 cells (1.3 fold each; FIGS. 3 and 4).

Thus, according to the invention a synergistic effect was observed in the combined sequential treatment of K562 cells with heat and ET-18-OCH3. It has to be noted that the order of the treatment: first heat shock, then recovery phase at about 37° C. followed by treatment with the alkyl-lysophospholipid in association with another recovery phase at about 37° C., is of substantial importance for success. In the reverse order and adding the alkyl-lysophospholipid during the hyperthermal treatment no synergistic effect will be obtained. The portion of Hsp70 localized at the plasma membrane was found to increase markedly (cf. FIG. 3) and this increase to reflect an increased sensitivity of the thus treated tumor cells for the lysis by NK cells (FIG. 5). Antibody blocking studies revealed that the increased lysis sensitivity correlates with the amount of membrane-bound Hsp70 (cf. FIG. 5). In untreated K562 cells or those treated with Tween 20, no increased lytic activity could be observed (data not shown).

CD34-positive progenitor cells or PBL cells which were shown to lack Hsp70 expression on their plasma membrane could not be lysed by NK cells either under physiological conditions or under the treatments performed according to the present invention under heat stress or heat and ET-18-OCH3 stress (cf. Table 4). This demonstrates the effect mediated by the method according to the invention to be a tumor-specific effect.

Besides the IL-2-stimulated NK-enriched cell population the cytotoxic activity of unstimulated resting NK cells (PBLs) of three HLA-distinct donors was investigated. The lysis patterns of all three HLA-distinct effector cell populations (A, B and C) were comparable (FIG. 6) and gave similar results to those obtained with IL-2 stimulated NK cells. In turn a heat treatment (2 hours, 41.8° C.) as well as a treatment with ET-18-OCH3 (25 µg/ml, 2 hours) followed by a recovery period of 2 hours at 37° C. of K562 cells resulted in a significant increase (about 1.4 fold) in lysis sensitivity wherein the lysis after treatment of K562 cells with a combination of heat shock and ET-18-OCH3 was increased in a synergistic manner by 2.1 fold. Since K562 cells are classical NK target cells which lack HLA class I expression, the increase in lysis sensitivity to unstimulated effector cells can be correlated with NK cells. Addition of IL-2 to NK cells enhances this activity. Nevertheless, Hsp70-specific NK cells could be obtained so far from all donors tested (>100). This finding could be demonstrated with more than 100 different donors. In all donors, a resting Hsp70-specific NK population could be detected.

Although most leukemic cells are sensitive to treatments with cytostatic and cytotoxic agents, it is known that some types of leukemic cells such as K562 cells are very resistant to the toxic effects of ET-18-OCH3. According to the invention it could be demonstrated that a combined sequential treatment of these leukemic cells with heat and ET-18-OCH3 in sublethal concentrations shows immunomodulatory activities which can be correlated with an increased translocation of Hsp70 to the plasma membrane of K562 cells. This increase in Hsp70 molecules expressed at the cell surface has a significant effect on the sensitivity of K562 tumor cells for lysis by NK cells. In addition, the actitivty of NK cells could be enhanced by Hsp70 on the membrane of tumor cells.

It has been known that in the treatment with ET-18-OCH3 alone a plasma membrane localization of Hsp70 without simultaneous stimulation of Hsp70 synthesis may be induced (5). However, it could be further demonstrated according to the present invention that tumor cells, in particular leukemic cells which otherwise are highly resistant against treatment with etherlipids exhibit a significantly better lysis by NK cells by a combined treatment with a heat shock and a sublethal concentration of ET-18-OCH3. This increased sensitivity for lysis by NK cells could be correlated with an increase in the expression of Hsp70 at the cell surface.

Thus, the studies carried out according to the present invention demonstrate that a combination of a heat treatment with the administration of a sublethal concentration of e.g. an etherlipid such as ET-18-OCH3 significantly increases the sensitivity of the target cells, e.g. of tumor cells, preferably of resistant leukemic cells, for example of K562 cells for the lysis by NK cells. This knowledge might also be used in the clinical field. Since normal PBL cells or CD34-positive progenitor cells do not express Hsp70 on their plasma membrane either under physiological conditions or following a heat treatment and/or a treatment with an etherlipid such a clinical use will be particularly useful since there is no risk for an autoimmune reaction. Healthy cells will not be lysed.

It could be demonstrated that the effectivity of a purging treatment in autologous bone marrow transplantation in patients with acute myeloic leukemia correlates with improved disease-free survival rates in vivo (6). Due to the investigations performed according to the present invention it will now be possible to combine the purging treatment with a heat treatment and a simultaneous treatment in a sublethal concentration with an alkyl-lysophospholipid such as ET-18-OCH3. By the increase in sensitivity of the leukemic cells which otherwise are resistant against treatment with an etherlipid as the sole purging agent to the lysis by NK cells the purging of bone marrow may be significantly improved. Furthermore, by the combination treatment suggested according to the invention of buffy coat cells (PBMCs or bone marrow cells) of leukemic patients but also of patients with solid tumors t he cell surface expression of Hsp70 on highly resistant leukemic cells or metastasing cells may be increased so that they may be lysed by NK cells specific for tumor cells expressing Hsp70. In addition, by the Hsp70 expressed in the plasma membrane the cytolytic activity of NK cells is increased.

In the following the materials and methods used with the experiments according to the present invention are explained in more detail. However they are contemplated as exemplary only and there are also other materials and methods available to practice the method of the present invention.

CELLS and CULTURE CONDITIONS

The human chronic myeloic leukemia cell line K562 was cultured in RPMI 1640 (Gibco, Eggenstein, Germany) medium conditioned with 10% heat-inactivated fetal calf serum (Gibco, Eggenstein, Germany) and containing 6 mM/l of L-glutamine and penicillin (100 IU/ml)/streptomycin (100 µg/ml) as ant ibiotics. The cells were kept in the exponential growth phase at a concentration of $1-2\times 10^6$ cells per ml of medium.

PREPARATIONS OF PERIPHERAL BLOOD LYMPHOCYTES (PBLs) AND PROGENITOR CELLS

Peripheral blood and umbilical cord blood was collected in sterile tubes. Following anti-coagulation with heparin (Heparin Novo, Novo Nordisk Pharma GmbH, Mainz, Germany) peripheral mononucleated blood cells (PBMCs) and umbilical cord lymphocytes were separated by density gradient centrifugation through Ficoll Isopaque (Ficoll Paque; Pharmacia, Uppsala, Sweden) and incubated in RPMI 1640 medium with 10% FCS at 37° C. overnight. PBLs of donors A, B, and C were also used as effector cells in the cytotoxicity test. As the target cells, PBLs of donors C, D, and E, and CD34-enriched progenitor cells from umbilical cord blood were kept in the same medium and treated as described below. An enrichment in CD34 cells was obtained using cell sorting in a FACSStar device (Becton Dickinson, Heidelberg, Germany). The percentage of cells with CD34-positive staining was determined by FACScan analysis as described below.

PRODUCTION OF ADHERENT NK EFFECTOR CELLS

Natural killer cells were obtained from PBLs from buffy coats derived from healthy human donors by Ficoll Isopaque (Pharmacia, Freiburg, Germany) density gradient centrifugation as described in (6). Shortly, PBLs ($3-5\times 10^8$) were separated into a non-adherent CD3+T cell fraction and an adherent NK-enriched cell fraction by incubation for 12 hours in plastic tissue culture flasks with RPMI 1640 medium containing recombinant IL-2 (100 IU/ml; Chiron, Frankfurt, Germany). The cell fraction enriched in NK cells was phenotypically characterized by flow cytometric analysis using double-stained anti-CD3/CD16+CD56 and C14/45 antibodies (Becton Dickinson, Heidelberg, Germany). A quantitative flow cytometric analysis was performed using a fluorescence-activated cell sorter (FACScan with PC Lysis II software, Becton Dickinson, Heidelberg, Germany). An effector cell population enriched in NK cells was used for cytotoxicity studies on day 4 after separation; the percentage of NK cells used in the cytotoxicity experiments was in the range of 40% to 60%.

HEAT TREATMENT AND TREATMENT WITH ALKYL-LYSOPHOSPHOLIPIDS

Exponentially growing K562 cells, CD34-enriched progenitor cells and PBLs were treated at the non-lethal temperature of 41.8° C. for 2 hours in a temperature-controlled water bath (Haake E3, Karlsruhe, FRG) and then incubated at 37° C. for 14 hours. 1-Octadecyl-methyl-rac-glycero-3-phosphocholine (ET-18-OCH3, edelfosine) was freshly dissolved in a 500 µg/ml stock solution in RPMI 1640 medium by heating to 50° C. for 30 minutes and three times sonication. Untreated or heat treated cells ($1\times 10^6$ cells/ml) were incubated with the non-toxic concentration of 25 µg/ml for 2 hours at 37° C. Following this treatment the cells were washed three times in 3× phosphate-buffered saline (PBS) and afterwards incubated in fresh culture medium without ET-18-OCH3 for further 2 hours at 37° C.

The non-lethal temperature of 41.8° C. and the non-toxic concentration of ET-18-OCH3 were determined by tests of the viability using trypane blue and propidium iodide and by measurements of apoptosis (cf. (5)).

The detergent polyoxyethylene sorbate 20 (Tween 20; Sigma, Munich, Germany) was employed as a membrane-active control agent in the non-lethal concentration of 5 ppm. A treatment of the cells with Tween 20 was carried out under identical conditions as those described for ET-18-OCH3.

PREPARATION OF MEMBRANES AND CYTOPLASM FRACTIONS

Plasma membrane separation was carried out following a slightly modified method according to Bauer and Hurtenbach (7) as described earlier (6). Shortly, $50\times 10^6$ cells either untreated or treated, were rinsed in ice-cold buffer (1 mM Tris-HCl, 5 MM $MgCl_2$, pH 7.4). The cell pellet was resuspended in ice-cold 3 mM phosphate-buffered sucrose solution (0.32 M, pH 7.6, 1 mM EDTA), and homogenized by 50 strokes with a tightly fitting piston in a Dounce homogenizer. Following centrifugation (2000 g, 40° C. for 15 minutes) the pellet was rehomogenized. The combined supernatants were sedimented at 11,000 g and 40° C. for 25 minutes. The resulting supernatant was centrifuged at 20,000 g at 40° C. for 45 minutes. The last pellet contained membranes and membrane-bound proteins and was resuspended in 100 µl of PBS.

To obtain the fractions of cytoplasmic protein, $5\times 10^6$ cells were lysed in 10 mM Tris-buffered saline (pH 7.5) containing 1% Nonidet P-40 (NP-40, Sigma) and 1 mM phenylmethylsulfonyl fluoride (PMSF, Sigma) for 45 minutes on ice diluted in Laemmli sample buffer.

SDS-PAGE AND WESTERN BLOT ANALYSIS

Equal amounts of protein (10 µg) were subjected to electrophoresis on a 10% SDS-PAGE as describe in (5) according to the method of Laemmli (8). Following SDS-PAGE electrophoresis the proteins were transferred to Immobilon PVDF membrane (Millipore Corp., Bedford, Mass.) using a standard protocol (9). Unspecific binding of the membrane was blocked with 5% skim milk in PBS. The blots were incubated for 1 hour each with primary Hsp70 antibody (Amersham, Braunschweig, Germany) and secondary antibody (goat-anti-mouse IgG peroxidase conjugate, BioRad, Germany). The immune complexes were detected using the ECL detection system (Amersham, Braunschweig, Germany).

Autoradiographs were quantified by laser densitometry (Ultrascan XL, Pharmacia, Freiburg, Germany). The relative amounts of Hsp70 were determined by the ratios of the area integrated under each peak to the untreated cells which were used as an internal standard.

CYTOTOXICITY TEST (CML)

The cytotoxicity test of the unstimulated PBLs and the effector cells enriched in NK cells was performed in a standard chromium 51 release assay for 4 hours (6). The target cells (K562 cells, PBLs or CD34-enriched progenitor cells) were incubated for 2 hours with 0.01 mCi/ml of Cr-51. After two washing steps the target cell number was determined, and the CML test was performed in 96-well microtiter plates at different effector-target ratios in the range of 30:1 to 3.5:1 NK cells or 60:1 to 15:1 for non-stimulated PBLs as the effector cells. The percentage of specific lysis was calculated as: [(experimental release—spontaneous release):(maximum release—spontaneous release)]×100. The percentage of spontaneous release was calculated as: (spontaneous release:maximum release)×100, and the percentage was always lower than 15% for every target cell.

The antibody blocking experiments were carried out using the Hsp70-specific monoclonal antibody RPN1197 (Amersham) in a concentration of 1 $\mu g/1\times10^6$ cells. The target cells were incubated with the antibody for 1 hour before labeling with Cr-51, and then the cytotoxicity test was carried out as described above.

STATISTICAL ANALYSIS

The significance of the differences between the different experimental values were evaluated using the Student's t test.

REFERENCES (1) Heesbeen E C., Rijksen G., van-Heugten H G., Verdonck L F.: Influence of serum levels on leukemic cell destruction by the ether lipid ET-18-OCH3. Leuk. Res. 19: 417, 1995
(2) Okamoto S., Olson A C., Berdel W E., Vogler W R.: Purging of acute myeloid leukemic cells by ether lipids and hyper-thermia. Blood 72: 1777, 1988
(3) Fujiwara K., Modest E J., Welander C E., Wallen C A.: Cytotoxic interactions of heat and an ether lipid analogue in human ovarian carcinoma cells. Cancer Res. 49: 6285, 1989
(4) Fujiwara K., Modest E J., Wallen C A.: Cell kill and cytostasis by ET-18-OCH3 and heat. Anticancer Res. 15: 1333,
(5) Botzler C., Kolb H J., Issels R D., Multhoff G.: Noncytotoxic alkyl-lysophospholipid treatment increases sensitivity of leukemic K562 cells to lysis by natural killer (NK) cells. Int. J. Cancer 65: 633, 1996
(6) Multhoff G., Botzler C., Wiesnet M., Eissner G., Issels R.: CD3 large granular lymphocytes recognize a heat-inducible imunogenic determinant associated with the 72-kD heat shock protein on human sarcoma cells. Blood 86: 1374, 1995
(7) Bauer H C., Hurtenbach U.: Murine cortical brain cells are autoantigenic from a distinct developmental stage onwards. JN. 12: 1, 1986
(8) Laemmli UK.: Cleavage of structural proteins during the assembly of the head of bacteriophage T4. Nature 227: 680,
(9) Towbin H., Staehelin T., Gordon J.: Electrophoretic transfer of proteins from polyacrylamide gels to nitrocellulose sheets: procedure and some applications. Proc. Natl. Acad. Sci. USA 76: 4350, 1979
(10) Berdel, W. E.: Membrane interactive lipids as experimental anticancer drugs, Brit. J. Cancer 64:208–211,1991

TABLES

Table 1. Viability of leukemic K562 cells compared to PBL and CD34 positive progenitor cells derived from healthy donors after combinatorial treatment with a nonlethal heat dose (41.8° C., 2 h) and ET-18-OCH3 or Tween 20 at different concentrations.

| Treatment hs+ | Surviving fraction (% ± SD) | | | Treatment | Surviving fraction (% ± SD) | |
|---|---|---|---|---|---|---|
| ET-18-OCH3 | K562 cells | PBL | CD34 cells | hs+ Tween20 | K562 cells | PBL |
| 100 µg/mL | 2 ± 2 | 0 | 0 | 1000 ppm | 3 ± 1 | 0 |
| 75 µg/mL | 35 ± 7 | 0 | n.t. | 500 ppm | 32 ± 5 | 16 ± 3 |
| 50 µg/mL | 80 ± 5 | 90 ± 6 | n.t. | 10 ppm | 69 ± 4 | 95 ± 2 |
| 25 µmg/mL | 97 ± 3 | 95 ± 4 | 88 ± 2 | 5 ppm | 99 ± 1 | 98 ± 2 |
| 10 µg/mL | 98 ± 2 | 98 ± 2 | 96 ± 5 | 1 ppm | 97 ± 2 | 98 ± 2 |

The viability is indicated as the percentage of surviving cells and determined by trypan-blue dye-exclusion assays. CD34 positive progenitor cells were not treated with Tween 20 since the amount of separated cells of one donor was not sufficient for all assays. The data represent the mean values of three independent experiments n.t. means not tested.

Table 2. Membrane expression of hsp70 on PBL and CD34 positive progenitor cells (purity was greater 90%) either untreated or following treatment with ET-18-OCH3 (25 µg), heat (41.8° C. 2 h) or heat plus ET-18-OCH3. The results are expressed as the difference in the percentage of hsp70 positively stained minus the percentage of cells stained with an isotype-matched control antibody. Only viable, propidium-iodide negative cells were analysed on a FACScan instrument. The data represent the mean of three independent experiments ± standard deviation (SD).

| Treatment | PBL | CD34 cells |
|---|---|---|
| untreated | 1.0 ± 1.1 | 1.86 ± 1.4 |
| ET-18-OCH3 (25 µg) | 1.1 ± 0.7 | 1.30 ± 0.5 |
| heat (41.8° C.) | 2.8 ± 1.2 | 1.37 ± 0.6 |
| heat and ET-18-OCH3 | 1.8 ± 0.9 | 1.73 ± 1.3 |

Table 3. Calculation of the specific differences in lysis of K562 cells either untreated (untr), heat treated (hs), ET-18-OCH3 treated or heat and ET-18-OCH3 treated.

| Treatment | ratio of lysis mean values ± SD | p values |
|---|---|---|
| untr/Tween20 | 1.180 ± 0.241 | 0.271 |
| untr/ET-18-OCH3 | 1.341 ± 0.023* | 0.032 |
| untr/hs | 1.316 ± 0.026* | 0.006 |
| untr/ hs + Tween20 | 1.300 ± 0.122 | 0.124 |
| untr/hs + ET-18-OCH3 | 1.845 ± 0.214* | 0.004 |
| heat/hs + Tween20 | 1.001 ± 0.064 | 0.300 |
| heat/hs + ET-18-OCH3 | 1.325 ± 0.072* | 0.006 |

The data represent the mean of 3 experimental values±standard deviation (SD); indicates values that are significantly (p<0.05) different from control levels by Student's t-test.

Table 4. Calculation of the specific differences in lysis of PBL and CD34-enriched cells (CD34 positive cells was ranging between 25% and 45%) either untreated (untr) or heat and ET-18-OCH3 treated.

| Treatment | ratio of lysis of PBL mean values ± SD | ratio of lysis of CD34 cells mean values ± SD |
|---|---|---|
| untr/hs | 0.98 ± 0.21 | 1.18 ± 0.12 |
| untr/hs + ET-18-OCH3 | 1.01 ± 0.11 | 1.08 ± 0.20 |
| heat/hs + ET-18-OCH3 | 1.09 ± 0.09 | 1.13 ± 0.15 |

The data represent the mean of 2 experimental values±standard deviation (SD).

What is claimed is:

1. A method of treating cells NX ex vivo, the method comprising, in order of recitation, heat treating a suspension comprising NK cells and target cells, at a temperature of about 38° C. to 43° C. for a period of at least one hour;

lowering the temperature of the suspension to about 37° C. for at least one hour;

adding a compound to the suspension in an amount sufficient to thereby increase expression of membrane-bound Hsp70 in the target cells, wherein the compound is present in the suspension in a sublethal amount for at least 30 minutes; and incubating the NK cells and target cells at 37° C. for at least one hour.

2. The method of claim 1, wherein the target cells are selected from the group consisting of leukemic cells, metastasized solid tumor cells, HIV-infected cells, mycobacterium-infected cells, and combinations thereof.

3. The method of claim 2, wherein the target cells are K562 cells.

4. The method of claim 2, wherein the target cells are metastasized cells from a tumor selected from the group consisting of a carcinoma, sarcoma, melanoma, lymphoma, and combinations thereof.

5. The method of claim 1, wherein the compound is an alkyl-lysophospholipid.

6. The method of claim 1, wherein the compound is edelfosine.

7. The method of claim 1, wherein the heat treatment is performed at a temperature of about 39° C. to 42° C.

8. The method of claim 1, wherein the heat treatment is performed at a temperature of about 41° C. to 42° C.

9. The method of claim 1, wherein the compound is added to achieve about 1 to 30 μg/ml concentration of the compound in the suspension.

10. The method of claim 1, wherein the compound is added to achieve about 10 to 25 μg/ml concentration of the compound in the suspension.

11. The method of claim 1, wherein the heat treatment is performed for about 1 to 3 hours.

12. The method of claim 1, wherein the heat treatment is performed for about 2 to 3 hours.

13. The method of claim 5, wherein the heat treatment is performed for about 30 minutes to 3 hours.

14. The method of claim 5, wherein the heat treatment is performed for about 1 hour to 2 hours.

15. The method of claim 1, wherein the NK cells exhibit a property selected from the group consisting of CD16-negative, IL-2 dependent growth, CD3-negative, α/β T cell receptor-negative, γ/δ T cell receptor-negative, MHC type-independent killing, and combinations thereof.

16. The method of claim 1, wherein the lowering step and incubation are performed for about 2 to 16 hours.

17. The method of claim 1, wherein the lowering step and incubation are performed for about 8 to 12 hours.

18. The method of claim 1, wherein the suspension comprises buffy coat cells derived from whole blood.

19. A method of treating a subject having cancer or an infection, the method comprising treating NK cells ex vivo according to the method of claim 1; and administered the treated NK cells to the subject.

20. The method of claim 19, wherein the expression of Hsp70 on the cell membrane of target cells has been increased relative to before treatment of the cells ex vivo.

* * * * *